US012793215B2

(12) United States Patent
Lu et al.

(10) Patent No.: US 12,793,215 B2
(45) Date of Patent: Nov. 10, 2026

(54) RECONSTRUCTION OF ENTRANCE PUPILS USING IMAGE DATA

(71) Applicant: Lemon Inc., Grand Cayman (KY)

(72) Inventors: Chien Hung Lu, Los Angeles, CA (US); Bowei Zhang, Los Angeles, CA (US); Runyu Liu, Los Angeles, CA (US); Eric Kok Thong, Los Angeles, CA (US)

(73) Assignee: Lemon Inc., Grand Cayman (KY)

(*) Notice: Subject to any disclaimer, the term of this patent is extended or adjusted under 35 U.S.C. 154(b) by 236 days.

(21) Appl. No.: 18/592,339

(22) Filed: Feb. 29, 2024

(65) Prior Publication Data

US 2025/0278830 A1 Sep. 4, 2025

(51) Int. Cl.
*G06T 7/00* (2017.01)
*G16H 30/40* (2018.01)

(52) U.S. Cl.
CPC ........... *G06T 7/0012* (2013.01); *G16H 30/40* (2018.01); *G06T 2207/10012* (2013.01); *G06T 2207/30041* (2013.01)

(58) Field of Classification Search
CPC ..................... G06T 7/0012; G06T 7/73; G06T 2207/10012; G06T 2207/30041; G16H 30/40
See application file for complete search history.

(56) References Cited

U.S. PATENT DOCUMENTS

| | | | | | |
|---|---|---|---|---|---|
| 6,152,563 | A * | 11/2000 | Hutchinson | G06F 3/013 351/209 |
| 8,824,779 | B1 * | 9/2014 | Smyth | G06T 7/73 382/117 |
| 10,061,383 | B1 * | 8/2018 | Ludusan | G06V 10/42 |
| 2016/0007849 | A1 * | 1/2016 | Krueger | A61B 5/1128 600/301 |
| 2019/0243448 | A1 * | 8/2019 | Miller | A61B 3/113 |
| 2022/0377312 | A1 * | 11/2022 | Samples | H04N 13/344 |
| 2023/0400917 | A1 * | 12/2023 | Lundahl | G06T 7/73 |
| 2025/0014221 | A1 * | 1/2025 | Hudson | G06T 7/73 |

OTHER PUBLICATIONS

Fedtke et al. "The entrance pupil of the human eye: a three-dimensional model as a function of viewing angle." Optics express 18.21 (2010): 22364-22376. (Year: 2010).*

(Continued)

*Primary Examiner* — Katrina R Fujita
(74) *Attorney, Agent, or Firm* — Alleman Hall LLP

(57) ABSTRACT

Implementations of reconstruction of entrance pupils of the human eye are provided. One aspect includes a device comprising a camera system and processing circuitry coupled to memory storing instructions that, when executed by the processing circuitry, causes the processing circuitry to receive image data from the camera system, and extract a set of features from the image data. Extracting the set of features comprises classifying the features into a plurality of feature types. The processing circuitry is further configured to calculate a set of feature measurements from the extracted set of features, and perform an entrance pupil reconstruction process for determining entrance pupil position data using the set of feature measurements.

20 Claims, 11 Drawing Sheets

(56) References Cited

OTHER PUBLICATIONS

Lu et al. "Neural 3D gaze: 3D pupil localization and gaze tracking based on anatomical eye model and neural refraction correction." 2022 IEEE international symposium on mixed and augmented reality (ISMAR). IEEE, 2022. (Year: 2022).*

Guestrin, E. D. et al., "General Theory of Remote Gaze Estimation Using the Pupil Center and Corneal Reflections," IEEE Transactions on Biomedical Engineering, vol. 53, No. 6, Jun. 2006, 10 pages.

* cited by examiner

RECONSTRUCTION OF ENTRANCE PUPILS USING IMAGE DATA

BACKGROUND

Extended reality (XR) applications, such as applications in augmented reality (AR), virtual reality (VR), and mixed reality (MR), often employ the use of head-worn devices to provide the user with digital information that combines with, or replaces, the physical world to give the user an immersive experience. An accurate presentation of the digital information to the user's eye(s) relies on various aspects, including knowledge of the projection optics and characteristics/location of the user's eye(s).

SUMMARY

Implementations of reconstruction of entrance pupils of the human eye are provided. One aspect includes a device comprising a camera system and processing circuitry coupled to memory storing instructions that, when executed by the processing circuitry, causes the processing circuitry to receive image data from the camera system, and extract a set of features from the image data. Extracting the set of features comprises classifying the features into a plurality of feature types. The processing circuitry is further configured to calculate a set of feature measurements from the extracted set of features, and perform an entrance pupil reconstruction process for determining entrance pupil position data using the set of feature measurements.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

Figure 1:
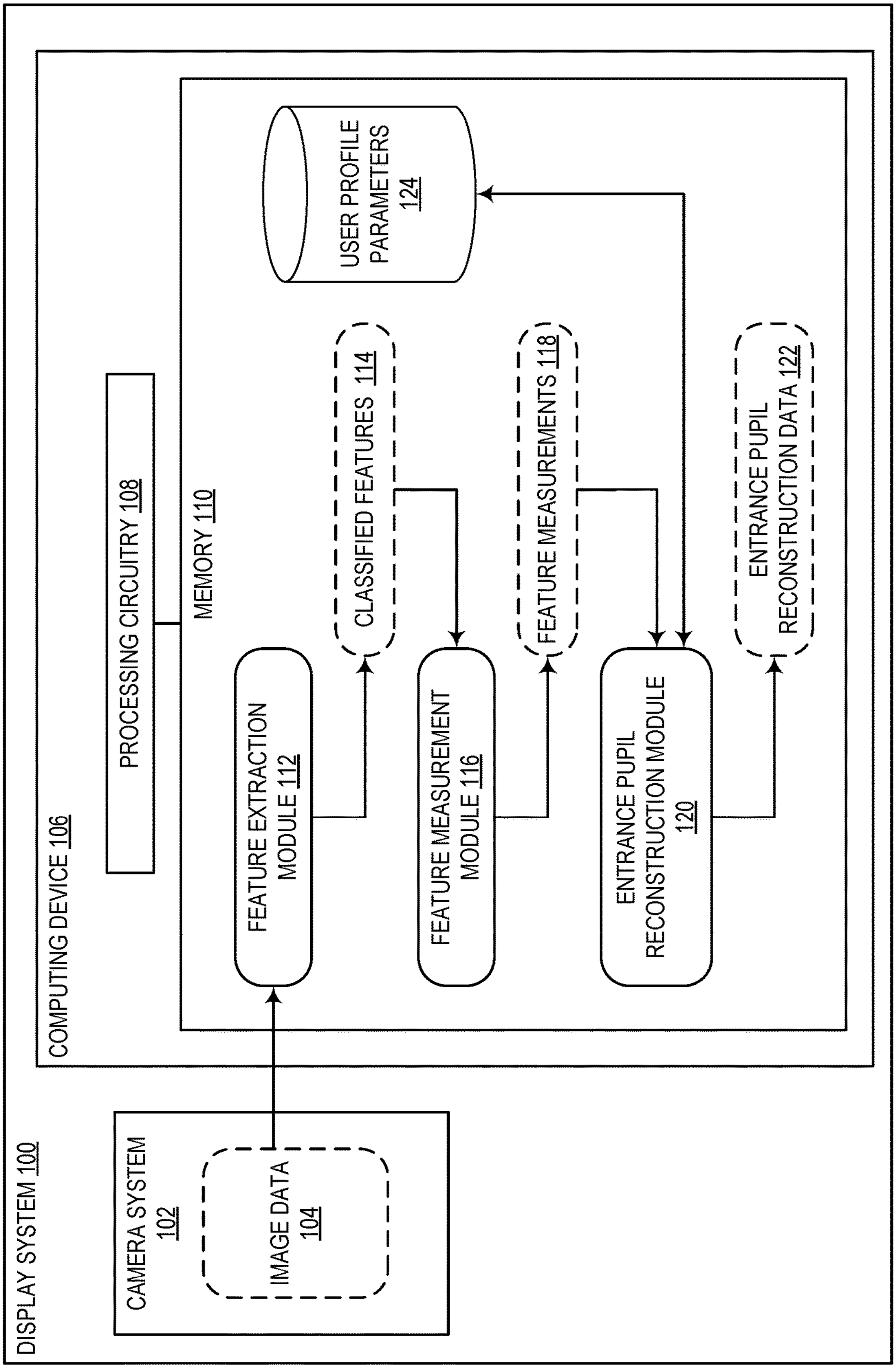
FIG. 1 shows a schematic view of an example display system for reconstructing an entrance pupil of a human eye.

Performance of XR systems (e.g., head-worn eye displays) in projecting digital information to the user's eye(s) can depend on various factors. Generally, projection of digital information in XR systems is limited in performance by the amount/efficiency of projected light reaching the user's eye(s). For example, a projection system of an XR system projecting digital images to areas in which the user cannot physically see results in light inefficiency. As such, knowledge of entrance pupils and exit pupils in such applications can provide for more accurate and efficient configurations. In addition to image projection, various other applications can benefit from such knowledge, including but not limited to dynamic distortion compensation and dynamic color compensation.

Current methods of configuring XR systems to accommodate a user's entrance pupil(s) include naïve implementations where eye parameters are assumed and fixed to derive an entrance pupil with which to configure various applications. Eye parameters can refer to invariant eye properties during the use of XR systems. For example, pupil-cornea distance, pupil size, and/or cornea curvature are often assumed in XR systems. Generally, average or median parameter values of a population are utilized as the assumed parameters. However, such methods can vary in performance among users as the assumed parameters do not accurately represent the population, resulting in reconstruction errors. Users with eye features deviating from the average/median may suffer poor performance. Furthermore, current methods of reconstructing entrance pupils are based on a single point abstraction. However, the entrance pupil is a three-dimensional shape, and, as such, single-point abstraction does not provide a precise optical simulation. Other methods of providing entrance pupil information include initial calibration of a user's eye parameters, which can be used to derive the entrance pupil. However, during use of a XR system (e.g., smart glasses), the user's eye(s) and, consequently, the entrance pupil may move with respect to the XR system. In such cases, the ability to gather real-time knowledge of the user's eye position may be advantageous in correcting runtime errors.

In view of the observations above, systems and methods for reconstructing entrance pupils of the human eye using image data are provided. Briefly, a parameter-free methodology without relying on assumptions of the user's eye parameters can be implemented to reconstruct an entrance pupil using image data to provide a robust methodology that covers a larger population coverage compared to methodologies utilizing assumed eye parameters. Image data from a camera system configured to image a user's eye(s) can be provided in real-time. For example, a head-worn XR system can include embedded cameras configured to image one or both of the user's eyes. As such, the reconstruction of entrance pupils can also be performed in real-time, allowing for self-calibration and more accurate entrance pupil reconstruction over time.

Entrance pupil reconstruction can be performed in various ways. In some implementations, the provided image data of the user's eye(s) is analyzed, and features of the user's eye(s) can be extracted. The extracted features can be classified into various feature types corresponding to eye features, including but not limited to pupils, glints, and limbi. Once classified, the features can be measured to provide feature measurements used to derive an entrance pupil position corresponding to the eye from which the image data is taken. In some implementations, the feature measurements are assessed quantitatively and/or qualitatively to determine their effective use in the entrance pupil reconstruction process. Assumed parameters or previously saved parameters can be used in lieu of missing features (or poor-quality features). The derived entrance pupil position data can then be used for various XR applications, including those described in the sections above.

Turning now to the drawings, entrance pupil reconstruction methodologies are described in further detail. FIG. 1 shows a schematic view of an example display system 100 for reconstructing an entrance pupil of a human eye. The example display system 100 includes a camera system 102 for providing image data 104 with which to reconstruct the entrance pupil. The example display system 100 can be any display system in which entrance pupil position data is utilized to provide various optical applications, including but not limited to dynamic distortion compensation and dynamic color compensation. For example, the example display system 100 can be a head-worn display device, such as a heads-up display system, smart glasses, etc.

The camera system 102 can be implemented in various ways. Different types of cameras, such as but not limited to visible and infrared cameras, can be utilized. The camera system 102 includes a camera configured to image an eye of the user. In some implementations, the camera system 102 includes two cameras for imaging an eye of the user, providing stereoscopic image data for said eye. Similar implementations can be provided for each eye of the user (e.g., two cameras individually capturing respective image data for both eyes of the user, or two sets of two cameras capable of providing stereoscopic image data for both eyes of the user).

In the depicted example of FIG. 1, the entrance pupil reconstruction process is performed by a computing device 106 of the example display system 100. Any type of computing device can be implemented. In the example display system 100, the computing device 106 includes processing circuitry 108 and memory 110 storing instructions that, when executed by the processing circuitry 108, causes the processing circuitry 108 to perform the various processes described herein. The process includes receiving the image data 104 provided by the camera system 102. The image data 104 can be of various formats. For example, a camera system 102 implemented using a visible camera can provide image data 104 that includes RGB images. In some implementations, the image data 104 includes more than one image for a given eye, which can provide stereoscopic views of the given eye. The processes described herein are described with respect to one eye of the user but can be implemented similarly for the second eye. For example, the image data 104 can include images of both eyes of the user.

The computing device 106 includes a feature extraction module 112 for performing a feature extraction process on the received image data 104. The feature extraction process can include extracting a set of features from the image data 104 and classifying the features into a plurality of feature types, resulting in a set of classified features 114. Different feature types corresponding to eye features, such as but not limited to pupil, glint, and limbus, can be utilized for classification. A feature measurement module 116 can be implemented for performing a feature measurement process to calculate a set of feature measurements 118 from the set of classified features 114. The set of feature measurements 118 can include feature measurements of various feature types. For example, the set of feature measurements 118 can include one or more pupil feature measurements, one or more glint feature measurements, and/or one or more limbus feature measurements. In some implementations, the feature measurement module 116 is implemented to perform a quantity assessment and a quality assessment of the set of classified features 114.

An entrance pupil reconstruction module 120 can be implemented for performing an entrance pupil reconstruction process to determine entrance pupil position data 122 using the set of feature measurements 118. The entrance pupil position data 122 can include one or more entrance pupil positions that can be utilized for various applications by the example display system 100. The entrance pupil reconstruction process can be performed on feature measurements derived from image data containing mono or stereo images of a user's eye. The process can also be performed on feature measurements derived from image data containing images of both user's eyes. In some implementations, the entrance pupil position data 122 is determined using a ray-tracing process.

The entrance pupil reconstruction process can be performed in various ways, which can depend on the type and number of feature measurements 118 provided by the feature measurement model 116. For example, the entrance pupil reconstruction process can include reconstructing a pupil model, reconstructing a cornea model, reconstructing a limbus model, and/or determining a cornea refractive index using the various feature measurements provided. In some implementations, eye parameters stored locally for a given user, or assumed parameters (e.g., average or median parameters corresponding to the average or median eye features of a population), are used in lieu of certain feature measurements. For example, missing features or feature measurements of poor quality can be replaced with data from parameters retrieved from a database 124 storing parameters for user profile(s). After reconstructing an entrance pupil for a given user, parameters associated with the reconstructed entrance pupil can be used to update parameters stored in the database 124 storing parameters associated with one or more users.

In some implementations, the entrance pupil reconstruction process includes estimating a pupil position based on a two-dimensional pupil feature measurement derived from image data containing a mono-perspective image of a user's eye. The estimated pupil position can be used to determine a set of candidate entrance pupil positions. Different techniques can be used to select a candidate entrance pupil position from the candidates. In some implementations, a loss function is applied to a corresponding pupil shape for each of the candidate entrance pupil positions. The resulting loss values can be used to select the candidate entrance pupil position or to optimize the process in an iterative manner. For example, the candidate entrance pupil position corresponding to the pupil shape with the lowest loss value can be selected.

Figure 2:
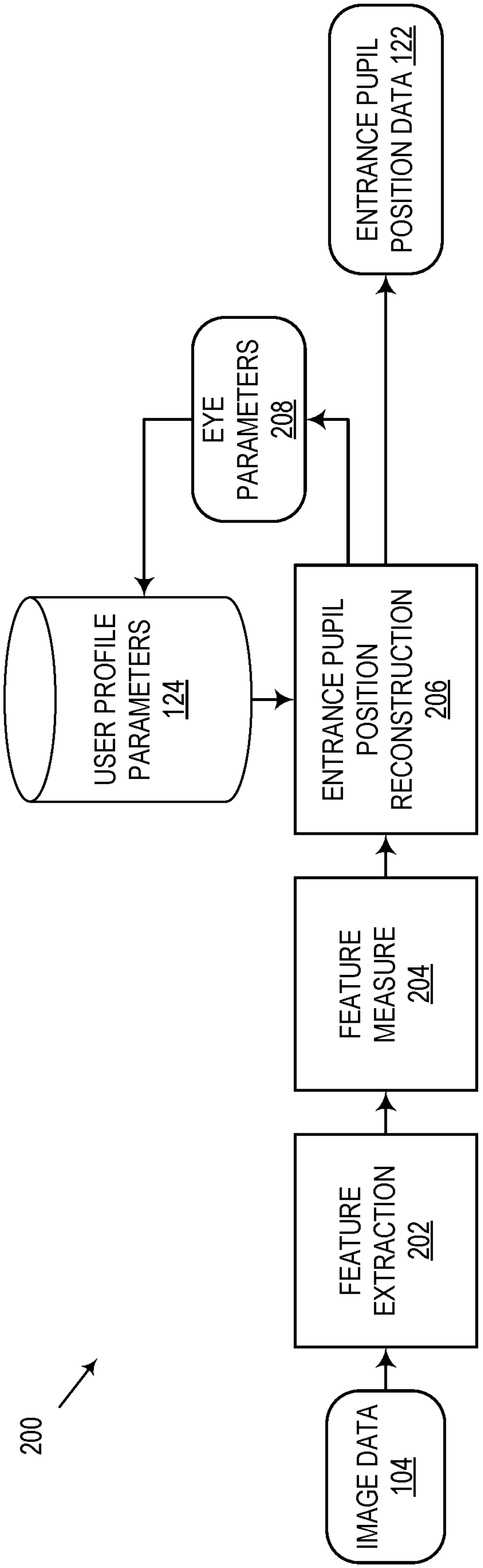
FIG. 2 shows a block model of an example process for converting image data into entrance pupil position data, which can be implemented using the example display system of FIG. 1.

FIG. 1 illustrates an overview of data flow through a method for converting image data 104 to entrance pupil position data 122. The different processes described can be performed in various ways, described below in further detail. FIG. 2 shows a block model of an example process 200 for converting image data into entrance pupil position data, illustrating a logical overview of said example process 200. The example process 200 starts with image data 104, which can be provided by various sources in various formats. For example, the image data 104 can be received from a camera system, such as the camera system 102 depicted in the example display system 100 of FIG. 1. Different camera systems can result in image data 104 with different formats (e.g., visible cameras can provide RGB images). The image data 104 can include one or more images of one or both eyes of the user. Depending on the content of the image data 104, different processes can be performed.

A feature extraction process 202 can be performed on the image data 104. For image data 104 containing more than one image, the feature extraction process 202 can be performed for each image in the image data 104. Various techniques can be implemented to perform the feature extraction process 202. In some implementations, an image segmentation network is implemented. For example, a neural network for performing image segmentation can be implemented to extract features from input images. Other techniques such as but not limited to edge detection, shape detection, image thresholding, etc. may also be utilized to perform feature extraction.

Once features are extracted, classification can be performed to label the extracted features with a feature type. Any feature type can be implemented. In some implementations, the extracted features are categorized into either a glint feature type, a pupil feature type, or a limbus feature type. Feature types of other eye features may also be utilized. Features not falling into any of pre-defined categories may be discarded, in some examples. Various techniques can be implemented to classify the features. For example, a neural network for classifying extracted features can be implemented.

After the feature extraction process 202, a feature measuring process 204 can be performed on the classified features to calculate a set of feature measurements. The feature measuring process 204 can be performed in various ways. In some implementations, the feature measuring process 204 includes a quantity assessment and a quality assessment of the classified features. For example, a count of each feature type can be performed, and quality of each feature can be ascertained. In some implementations, the quality assessment provides information to determine an effective count of each feature type, which can be used to determine which entrance pupil reconstruction methodology to employ. An example feature extraction process is depicted and described in FIG. 3 in further detail.

Continuing with the example process 200 of FIG. 2, an entrance pupil position reconstruction process 206 can be performed using at least the feature measurements calculated in the feature measuring process 204 to generate entrance pupil position data 122. The entrance pupil position data 122 can be formatted in various ways and include various components. In some implementations, the entrance pupil position data 122 includes data describing an entrance pupil position for a given eye of a user. In further implementations, the entrance pupil position data 122 includes two entrance pupil positions for both eyes of the user, respectively.

Various techniques and methodologies can be implemented in the entrance pupil position reconstruction process 206. Examples of entrance pupil position reconstruction processes are depicted and described in FIGS. 4-6 in further detail. In some implementations, the effective counts of the feature types can be utilized to determine the methodology implemented. For example, an effective count of more than two pupil features can indicate that the image data 104 contains stereoscopic image data, and a corresponding methodology for calculating entrance pupil position using stereoscopic images can be implemented. An example of a decision tree for deciding which methodology to implement based on effective counts of feature types is depicted and described in FIG. 7 in further detail.

The entrance pupil position reconstruction process 206 depicted in FIG. 2 can be performed using parameters to compensate for missing or poor-quality features from the image data 104. For example, parameters corresponding to the average or median eye features of a population can be utilized to substitute for missing or poor-quality features. In some implementations, parameters associated with a user profile retrieved from a database 124 storing such information are utilized. Such parameters can be generated from a calibration process and/or provided from previous entrance pupil position reconstruction processes. For example, eye parameters 208 determined through the entrance pupil position reconstruction process 206 can be used to update the parameters database 124 for the user profile associated with the current user. The eye parameters utilized can include cornea profile (such as curvature, length of long and short axes, refractive index, etc.), pupil profile (such as shape, size at certain display brightnesses, etc.), limbus profile (such as shape, size, etc.), and various geometric relationships among the eye features described above (such as the distance between the cornea center and the pupil plan, the distance and normal vector between the limbus and the pupil, the distance between the cornea center and the limbus plan, etc.).

Figure 3:
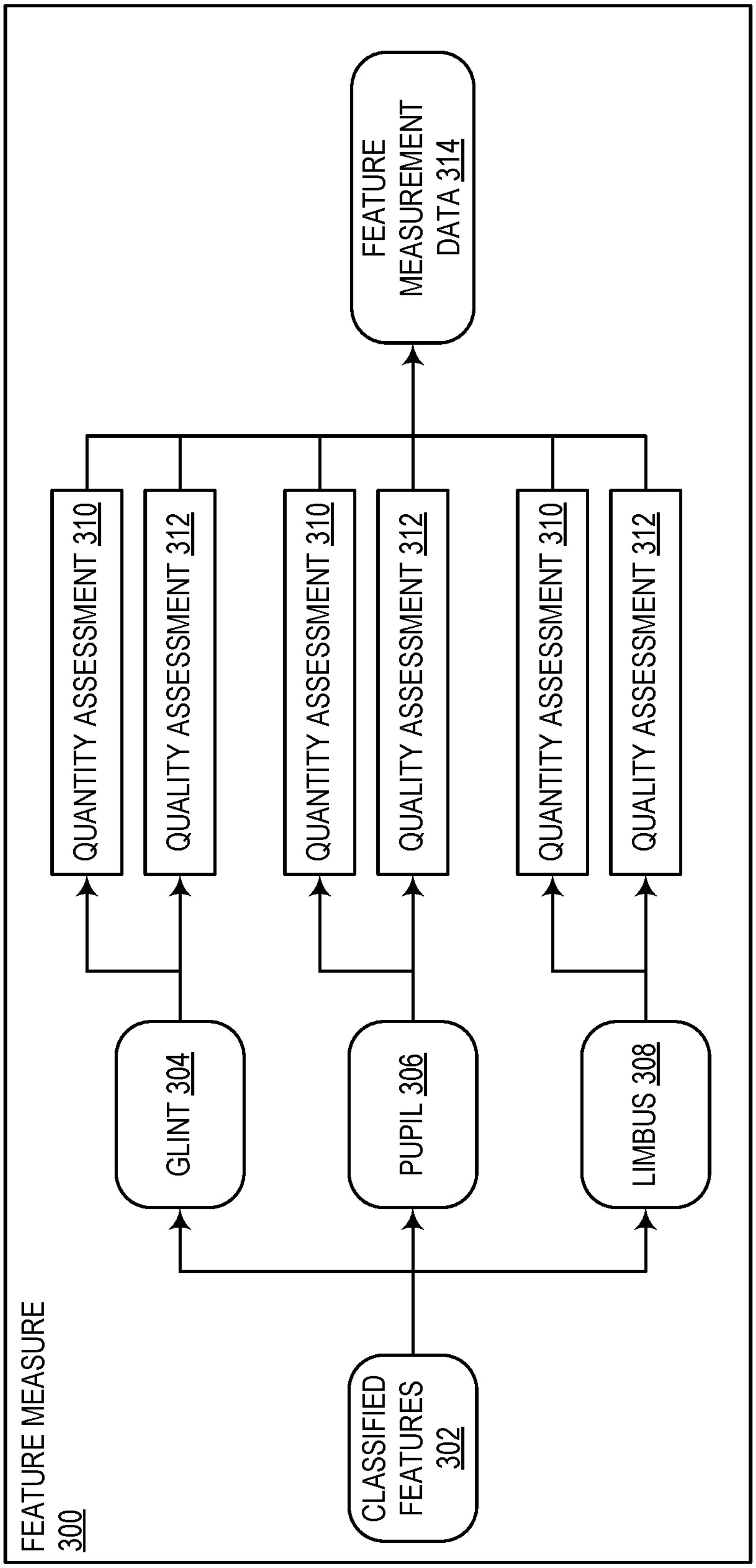
FIG. 3 shows a block model of an example feature measurement process, which can be implemented as part of the example process depicted in FIG. 2.

FIG. 3 shows a block model of an example feature measurement process 300. The example feature measurement process 300 can, for example, be implemented as the feature measurement process 204 described in FIG. 2. In the example depicted, the process 300 starts with a set of classified features 302, which includes three predefined classifications—glints 304, pupils 306, and limbi 308. Other feature types can also be implemented. For each feature type, a quantity assessment 310 and a quality assessment 312 can be performed. A quantity assessment 310 can be performed to provide a count of the number of each feature type detected. Quality assessment 312 can be performed to determine features with poor quality, which can provide an effective count of each feature type that can be used in determining which entrance pupil position reconstruction methodology to employ. The collective information from the quantity and quality assessments 310, 312 provides an output of feature measurement data 314.

Quality assessment 312 can be performed differently for different feature types. For glints, a quality assessment 312 can include determining whether a neighboring glint is too close. In some implementations, the quality assessment 312 for glints includes, for each $glint_i$, calculating its size ($s_i$) based on a Gaussian distribution. A nearest neighbor glint ($glint_j$) is located, and the distance ($d_{ij}$) between the two is calculated. For pupils, a quality assessment 312 can include calculating, for each pupil feature, its area as a percentage of the entire image ($o_i$). In some implementations, the quality assessment 312 for pupil features includes providing a confidence score ($pconf_i$), which can be provided by the feature extraction process. For limbus features, a quality assessment 312 can include calculating, for each limbus feature, its area as a percentage of the entire image ($l_i$). In some implementations, the quality assessment 312 for limbus features includes providing a confidence score ($lconf_i$), which can be provided by the feature extraction process.

In some implementations, the quality assessment 312 includes calculating effective counts for each of the feature types. Different methods can be utilized for different feature types. For example, the count of the glint features, provided by the quantity assessment, can be reduced for each glint i that is too close to a nearest neighbor glint j, resulting in an effective count for glint features. In some implementations, the neighboring glint j is considered too close if the distance between the glints ($d_{ij}$) is larger than the combined size ($s_i+s_j$) of the two glints. As a further example, the counts of the pupil and limbus features can each be reduced based on the sizes of the pupil features and the limbus features and/or their confidence levels not reaching a predetermined threshold (e.g., $o_i>0.01$ and $pconf_i>0.9$, and $l_i>0.01$ and $lconf_i>0.9$).

Figure 4:
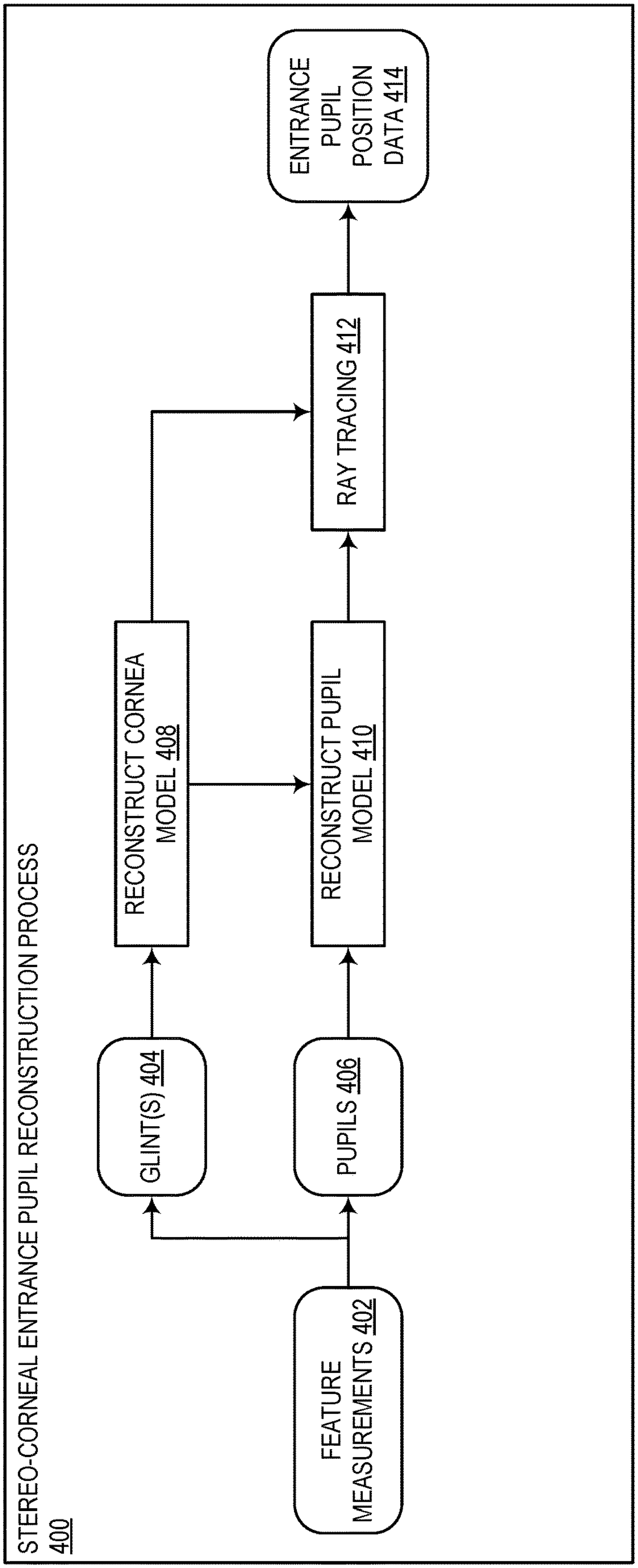
FIG. 4 shows a block model of an example stereo-corneal entrance pupil reconstruction process, which can be implemented as part of the example process depicted in FIG. 2.
Figure 5:
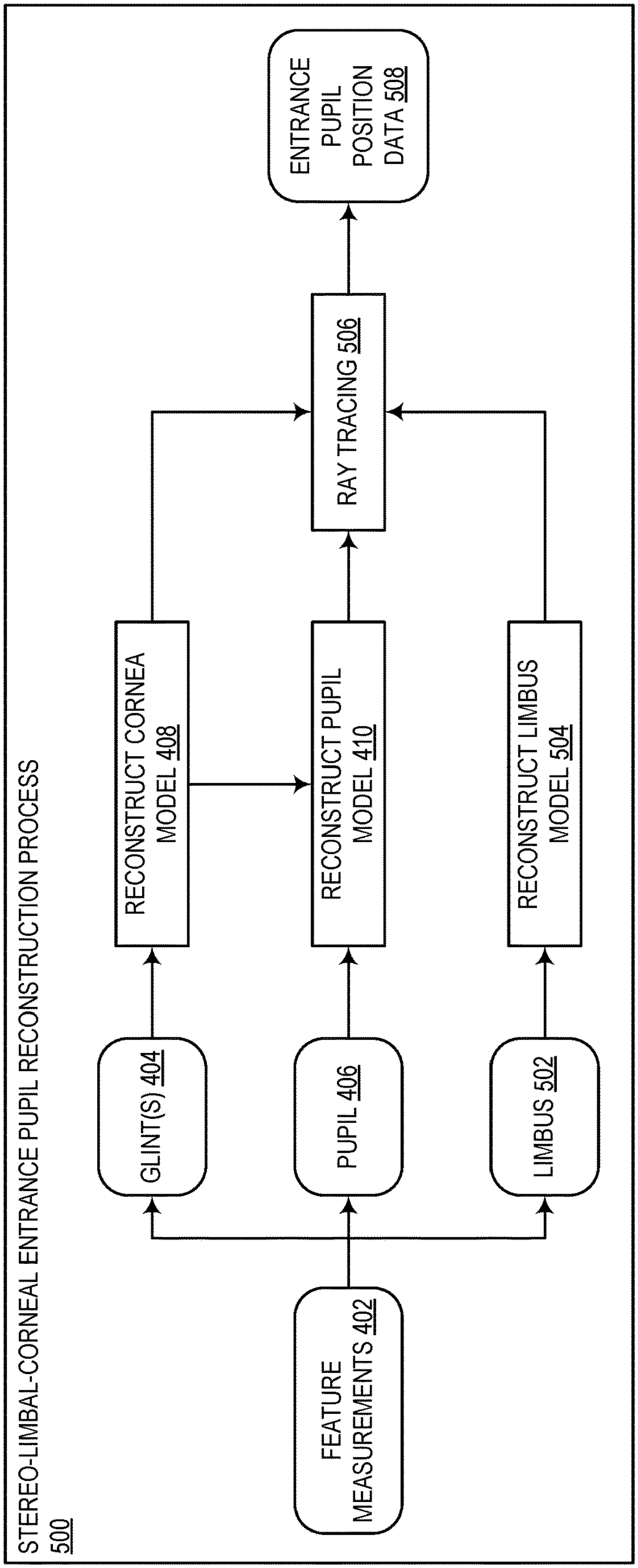
FIG. 5 shows a block model of an example stereo-limbal-corneal entrance pupil reconstruction process, which can be implemented as part of the example process depicted in FIG. 2.
Figure 6:
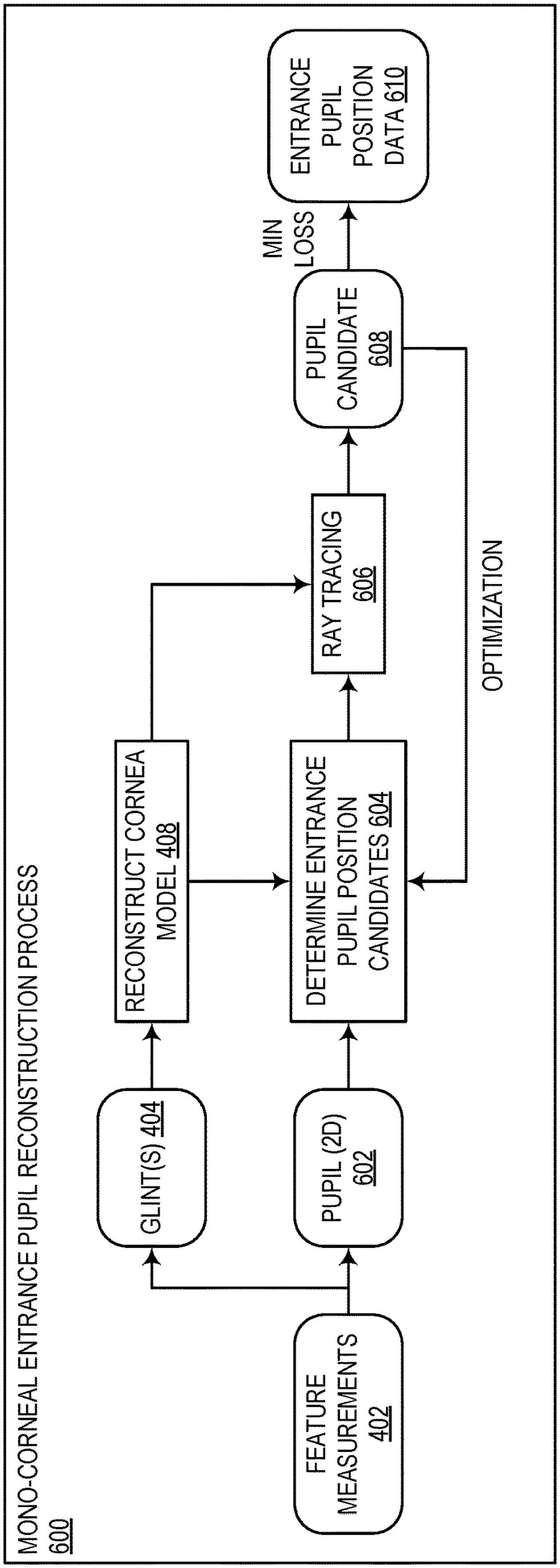
FIG. 6 shows a block model of an example mono-corneal entrance pupil reconstruction process, which can be implemented as part of the example process depicted in FIG. 2.
Figure 7A:
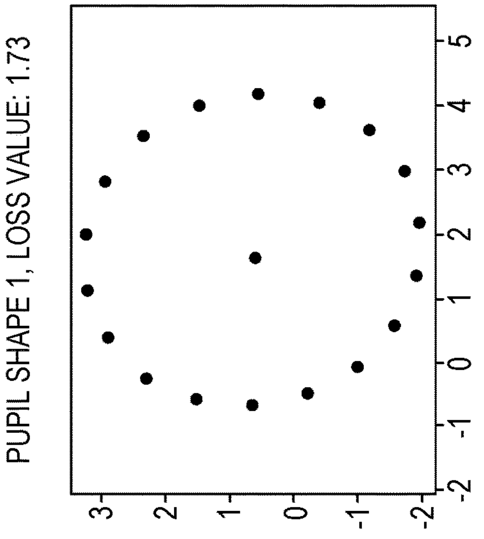
FIGS. 7A-7F show example pupil shapes derived from two-dimensional data of a pupil feature, which can be utilized in the example process depicted in FIG. 6.
Figure 7B:
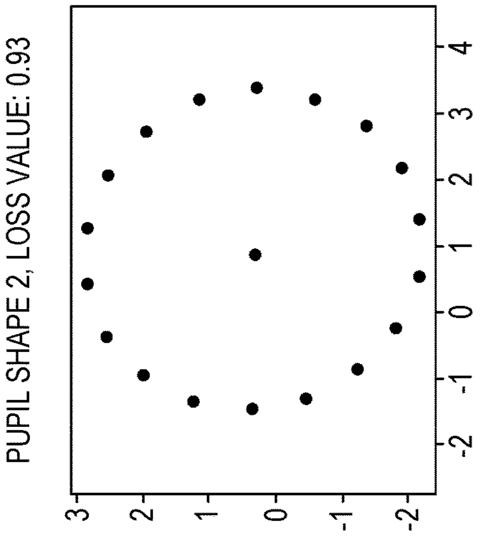
Figure 7C:
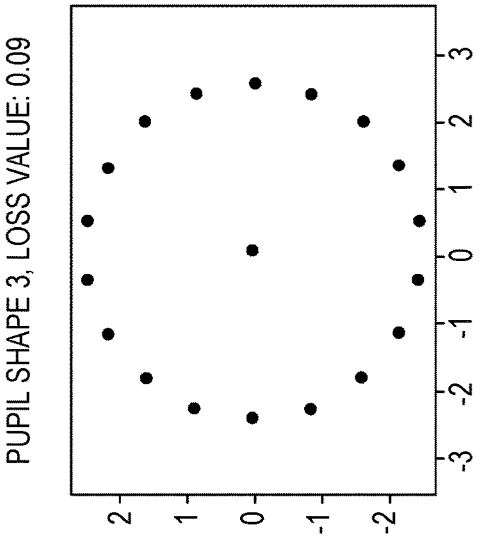
Figure 7D:
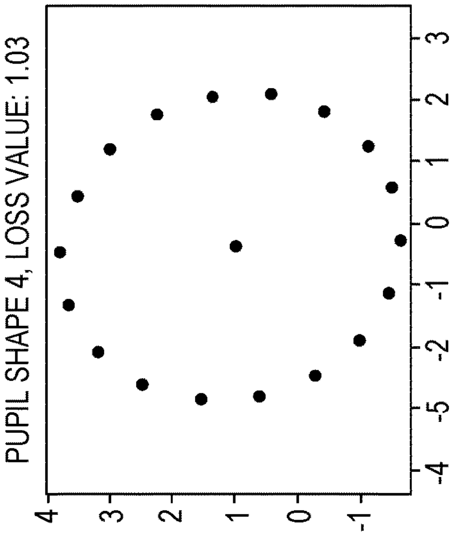
Figure 7E:
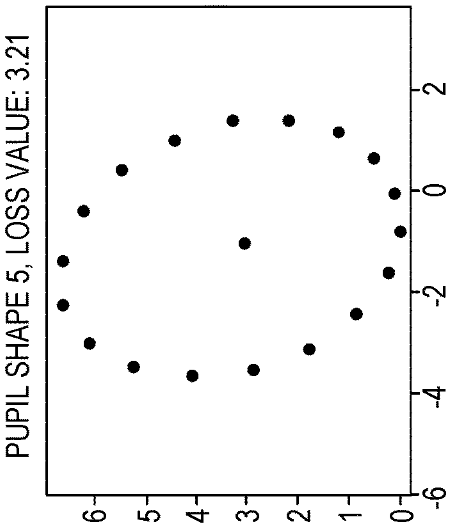
Figure 7F:
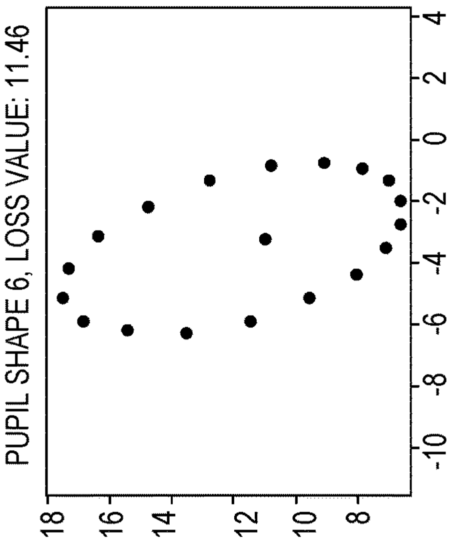

The effective count can be utilized for various purposes, including determining which entrance pupil reconstruction process to utilize. As described above, different entrance pupil reconstruction processes can be performed, the selection of which can depend on the type, quantity, and/or quality of feature measurements. For example, in cases where the effective count of pupil features is two, a stereo-process for analyzing image data containing stereo images is implemented. FIGS. 4-6 illustrates different entrance pupil reconstruction processes that can be performed based on different effective counts of certain feature types.

FIG. 4 shows a block model of an example stereo-corneal entrance pupil reconstruction process 400. The example process 400 can, for example, be implemented as the entrance pupil position reconstruction process 206 described in FIG. 2. In some implementations, the example stereo-corneal entrance pupil reconstruction process 400 is implemented when the effective count of pupil features is two (or at least two) and the effective count of limbus features is less than two. The example process 400 starts with a set of feature measurements 402 that is provided by a feature measuring process, for example. The feature measurements 402 include at least one or more glint measurements 404 and at least two pupil measurements 406.

The one or more glint measurements 404 can be used to perform a cornea model reconstruction process 408. The cornea model can be modeled as a three-dimensional ellipsoid given by the formula $$\frac{x'^2}{a^2} + \frac{y'^2}{b^2} + \frac{z'^2}{c^2} = 1.$$

$$X' = R(X - C),$$

where R, C is the rotational and translational matrices, respectively, and X'=(x', y', z'), X=(x, y, z). Depending on the number of glint measurements 404, a corresponding corneal model can be solved to estimate the cornea model. For example, when the number of glint measurements N=2/5/7, the cornea model reconstruction process 408 can be performed to reconstruct a sphere/oblate or prolate spheroid/ellipsoid, respectively. Generally, a larger number of glints can improve the stability of the cornea model reconstruction.

The pupil measurements 406 can be used to perform a pupil model reconstruction process 410. With stereo image data (from two cameras imaging one eye), the pupil model can be reconstructed with the cornea model reconstructed from the cornea model reconstruction process 408 described above. Parameters of the reconstructed pupil model can include, but are not limited to, pupil shape, pupil size (at the moment in which the image data is taken), and distance from the center of the cornea model.

The pupil model reconstruction process 410 can include determining two pupil position outlines $outline_{PP1}$ and $outline_{PP2}$, which can be obtained by cornea refraction (using the cornea model provided by the cornea model reconstruction process 408 discussed above. Reconstructing a pupil model can be performed by finding the intersection of the two pupil position outlines $outline_{PP1}$ and $outline_{PP2}$. This results in two possible solutions. To find the correct solution, the following conditions are considered. First, the correct solution is a two-dimensional plane (also termed as a pupil plan). The second condition includes validating that the vector p*c* is perpendicular to the pupil plan, where pupil center p* is defined as the geometric center of the intersection and the corneal center c* is defined using the cornea model described above.

A ray tracing process 412 can be performed using cornea and pupil models to determine entrance pupil position data 414. In some implementations, the example stereo-corneal entrance pupil reconstruction process 400 is performed on feature measurements 402 resulting from image data of two eyes, and the entrance pupil position data 414 includes entrance pupil positions for the two eyes. The ray tracing process 412 can include setting an observation point OP on one of the cameras for a given cornea and pupil center (derived from the cornea model and pupil model, respectively), allowing for a refractive point R1 to be calculated. The observation described herein can similarly applied to both cameras configured to capture stereoscopic images. The neighborhood of the observation point OP can be sampled in the camera plane (the normal vector is the camera pointing vector). Given the sampled neighborhood points $OP_i$ for i=0, 1, 2, 3, . . . , an entrance pupil position EPP can be calculated such that the following is satisfied. Lines from the EPP to $OP_i$ ($line_i$) are refracted by the cornea to form a refracted set of lines ($line'_i$). A point P can be defined as the nearest point to all $line'_i$, and d* can be defined as the root mean square distance from P to all $line'_i$. P and d* can be solved using pseudo inverse or least square methods for the following:

$$d^* = \sum_i d_i$$

$$\sum_i d_i^2 = \sum_i \left( (P - a_i)^T (P - a_i) - \left( (P - a_i)^T \hat{n}_i \right)^2 \right)$$

$$\left( \sum_i \left( I - \hat{n}_i \hat{n}_i^T \right) \right) P = \sum_i \left( I - \hat{n}_i \hat{n}_i^T \right) a_i$$

A point Q can be found on the $line_{EPP}$ line where Q=R1+ t*$line_{EPP}$·vector (where t is a one-dimensional parameter) such that ||P−p*|| is minimized. Accordingly, Q is the EPP with the following:

$$\arg\min_t \|P - p^*\|$$

For a static observation point, the observation point OP can be changed to a specified observation point. For dynamic observation points, corneal center c* (which can be provided by the reconstructed cornea model) and pupil center p* (which can be provided by the reconstructed pupil model) can be used to solve the optical axis of the eye. By placing the observation point OP on the optical axis, the entrance pupil position based on dynamic observation points can be obtained using the formulas described above.

With additional feature measurements and feature measurements of certain feature type, solving for the entrance pupil position can be performed more accurately. FIG. 5 shows a block model of an example stereo-limbal-corneal entrance pupil reconstruction process 500. The example process 500 can, for example, be implemented as the entrance pupil position reconstruction process 206 described in FIG. 2. In some implementations, the example stereo-limbal-corneal entrance pupil reconstruction process 500 is implemented when the effective counts of pupil features and limbus features are each two (or at least two). A portion of the example process 500 can be performed similarly as the process 400 described in FIG. 4, with respect to the use of glint features and pupil features for respectively reconstructing a cornea model and a pupil model. Additionally, with the provided limbus features 502, the process 500 further includes a limbus model reconstruction process 504.

Reconstruction of the limbus model can be performed by finding the intersection between the two limbus outlines ($outline_{limbus1}$ and $outline_{limbus2}$) provided by the limbus features 502. With multiple solutions, to find the correct one, the following conditions are considered. First, the correct solution is a two-dimensional plane (also termed as a limbus plan). The second condition is that the dot product between the normal vector of the limbus plan and pupil plan is minimal ($\min(N_{limbus}, N_{pupil})$). A cornea refractive index can be found such that the limbus plan and the pupil plane is aligned ($N_{limbus}=N_{pupil}$). The cornea refractive index can be used in a ray tracing process 506, in addition to the cornea model and the pupil model, to determine entrance pupil position data 508.

With two stereo cameras imaging an eye of the user and knowledge of the cameras' positioning, stereo information can be used to more accurately reconstruct a pupil model and/or a limbus model compared to image data from a mono camera. However, such data may be unavailable in some applications. For example, limited footprint, power, or cost budget may result in an XR device with only one imaging camera for each eye of the user. FIG. 6 shows a block model of an example mono-corneal entrance pupil reconstruction process 600. The example process 600 can, for example, be implemented as the entrance pupil position reconstruction process 206 described in FIG. 2. In some implementations, the example mono-corneal entrance pupil reconstruction process 600 is implemented when the effective count of pupil features is one and when a limbus feature is lacking. The example process 600 starts with a set of feature measurements 402 that is provided by a feature measuring process, for example. The feature measurements 402 include at least one or more glint measurements 404 and a pupil measurement 602. As there is only one effective pupil measurement 602, the pupil information is provided in two-dimensional information. The center of the pupil image J corresponds to the two-dimensional projection of the entrance pupil position onto the camera. $Line_{EPP}$ is obtained by back-projecting J, where $Line_{EPP}$ passes through the entrance pupil position. From the pupil measurement 602, a set of candidate entrance pupil positions are determined 604.

The glint measurement(s) 404 can be utilized similarly as described above with respect to FIG. 4 to perform a reconstruction process 408 of the cornea model. A ray-tracing process 606 can be performed using the reconstructed cornea model and the candidate entrance pupil positions candidates to select a corresponding pupil candidate 608 based on a loss function, which provides entrance pupil position data 610. The pupil candidate 608 can also be used to optimize the process for determining candidate entrance pupil positions.

The ray-tracing process 606 can include setting an observation point $OP_0$ at the camera pinhole position. The neighborhood of the observation point OP can be sampled in the camera plane (the normal vector is the camera pointing vector). Given the sampled neighborhood points $OP_i$ for i=0, 1, 2, 3, . . . , an entrance pupil position EPP can be calculated such that the following is satisfied. Lines from the EPP to $OP_i$ ($line_i$) are refracted by the cornea to form a refracted set of lines ($line'_i$) that intersects point P, the actual position of the pupil (PPP). Point P should be on $line'_0$ (where $line'_0$ is $line'_{PPP}$ and is $line'_{EPP}$ after refraction through the cornea model. Point P is the nearest point to all $line'_i$, and d* can be defined as the root mean square distance from P to all $line'_i$. P and d* can be solved using pseudo inverse or least square methods for the following:

$$d^* = \sum_i d_i$$

$$\sum_i d_i^2 = \sum_i \left((P - a_i)^T (P - a_i) - \left((P - a_i)^T \hat{n}_i\right)^2\right)$$

$$\left(\sum_i \left(I - \hat{n}_i \hat{n}_i^T\right)\right) P = \sum_i \left(I - \hat{n}_i \hat{n}_i^T\right) a_i$$

A point Q (which can be represented by a one-dimensional parameter t) can be found on the $line_{EPP}$ line such that d* is minimized.

$$\arg\min_t d^*$$

Point Q is then the EPP, and the corresponding P is the PPP.

In some implementations, pupil shape constraints are enforced. Pupil shape constraints can include but are not limited to pupil in a plane and geometric center invariance (point of focus=geometric center of pupil shape). An observation point OP can be set at the camera pinhole position. Then EPP=OP+t*$line_{EPP}$·vector, and $line_{EPP}$ generates refraction point A in the cornea model. The neighborhood of the observation point OP can be sampled, with $OP_i$ for i=0, 1, 2, 3, . . . Lines from the EPP to $OP_i$ ($line_i$) are refracted by the cornea to form a refracted set of lines ($line'_i$) that intersects point P, the actual position of the pupil (PPP). Using the method described above, point P can be determined. Let N=P−c, with c as the center of the cornea model. A plane PL:N*P=d can be obtained, where plane normal vector is N and one point on the plane is P. The image of the detected pupil edge point $e_i$ (i=1, 2, 3, . . . ) is inversely projected to get $pe_{line_i}$ (i=1, 2, 3, . . . ). The intersection of $pe_{line}$ in plane PL is $pe_{pt_i}$ (i=1, 2, 3, . . . ), where the geometric center of $pe_{pt_i}$ is pg. The loss function can then be defined as d*=||P−pg|| and d* can be minimized with respect to t (EPP=A+t*$line_{EPP}$·vector).

A mono-limbal-corneal entrance pupil reconstruction process can also be implemented as the entrance pupil position reconstruction process 206 described in FIG. 2. In some implementations, the mono-limbal-corneal entrance pupil reconstruction process is implemented when the effective counts of pupil features and limbus features are both one. A portion of the process can be implemented similarly as the stereo-limbal-corneal entrance pupil reconstruction process 500 of FIG. 5. Additionally, the limbus feature can be used in the entrance pupil reconstruction process. The center L of the limbus captured by the camera is inversely projected to obtain $line_{limbus}$. $Line_{EPP}$ produces a refraction point at the cornea model with $line_{PPP}$. A nearest point P of $line_{PP}$ and $line_{limbus}$ can be found as the intersection point. Point P can be set as the pupil center, and the pupil model can be reconstructed by the following steps. Let N=P−c, with c as the center of the cornea model. A plane PL:N*P=d can be obtained, where plane normal vector is N and one point on the plane is P. The image of the detected pupil edge point $e_i$ (i=1, 2, 3, . . . ) is inversely projected to get $pe_{line_i}$ (i=1, 2, 3, . . . ). The intersection of $pe_{line}$ in plane PL is $pe_{pt_i}$ (i=1, 2, 3, . . . ). $pe_{pts}$ provides the reconstructed pupil shape.

FIGS. 7A-7F show example pupil shapes derived from two-dimensional data of a pupil feature. The example pupil shapes are reconstructed for different candidate entrance pupil positions. As shown, the closer the shape is to being orthogonally symmetric, the smaller the loss function value. Other loss functions may also be implemented. For example, curvature, roundness, and other attributes may be considered for the loss function.

Figure 8A:
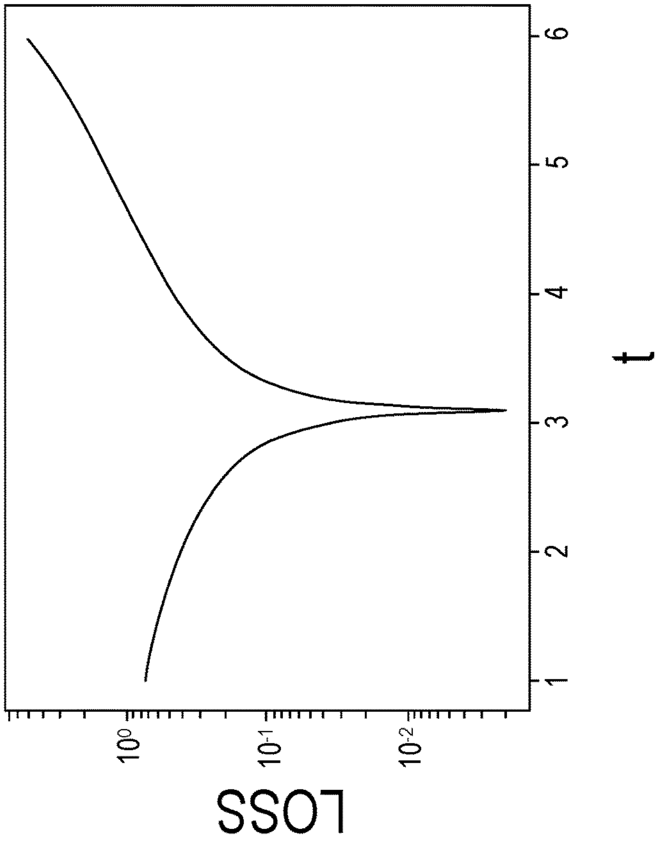
FIGS. 8A and 8B show charts of loss values and entrance pupil position error, respectively, for different pupil shapes, which can be utilized in the example process of FIG. 6.
Figure 8B:
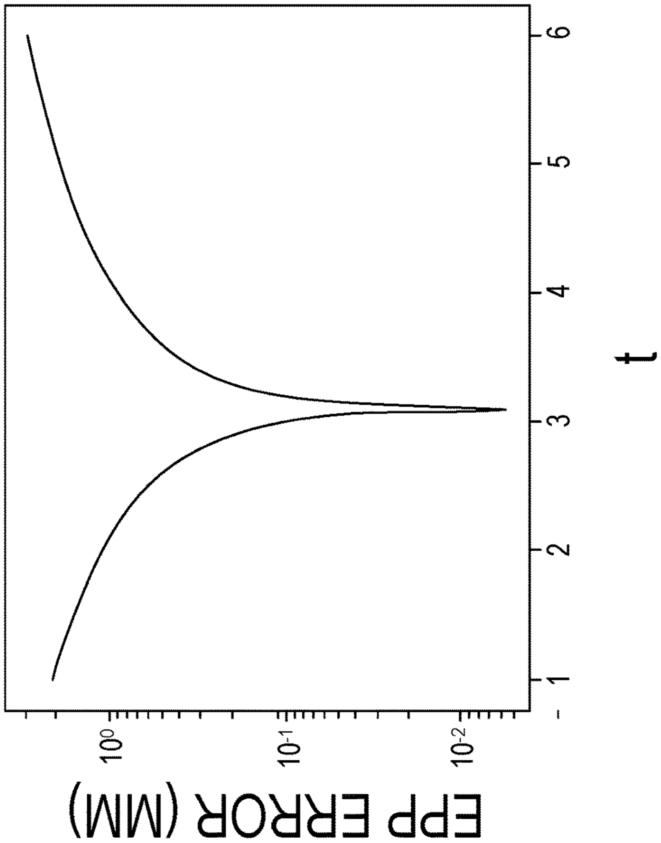

FIGS. 8A and 8B show charts of loss values and entrance pupil position error, respectively, for different pupil shapes. The data results illustrated are from an example XR system and is provided for conceptual purposes. The different pupil shapes, represented by the one-dimensional parameter t. In the depicted example, there is a minimum loss value found when t is approximately 3.094 (illustrated in FIG. 8A), indicating symmetry and corresponding to an entrance pupil position error minimum (illustrated in FIG. 8B) of approximately five micrometers.

Figure 9:
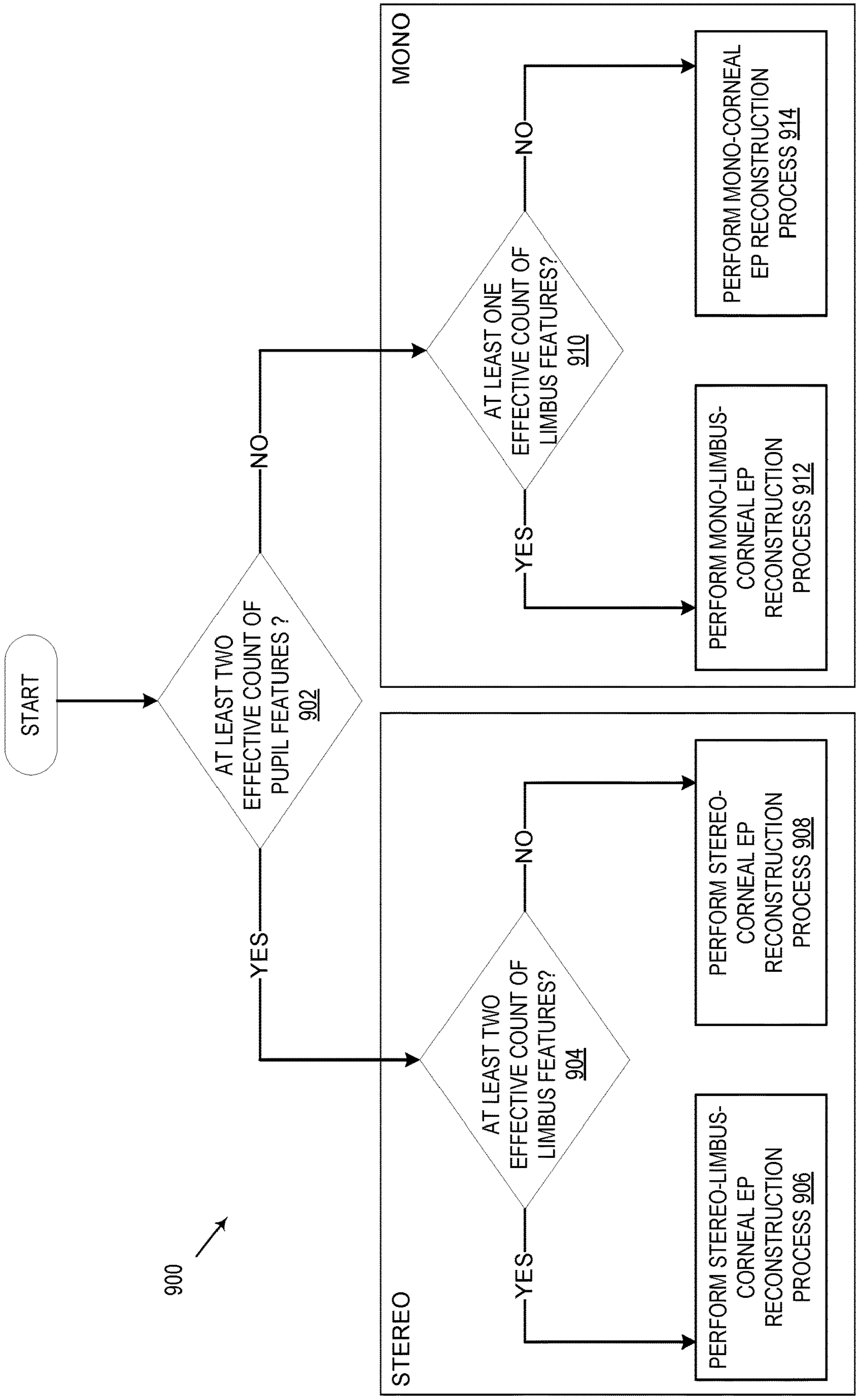
FIG. 9 shows a block diagram of an example decision process for determining which entrance pupil reconstruction process to perform, which can be implemented as part of the example process depicted in FIG. 2.

The various entrance pupil reconstruction processes described above, including those described in FIGS. 4-6, can be chosen for implementation depending on various factors. For example, different effective counts of various feature types can be used to determine which process to implement. FIG. 9 shows a block diagram of an example decision process 900 for determining which entrance pupil reconstruction process to perform. The process 900 starts with first determining the effective count of pupil features 902. If the effective count of pupil features is at least two, a class of stereo processes is implemented. In such cases, the decision process continues with a determination of the effective count of limbus features 904. If the effective count of limbus features is at least two, a stereo-limbus-corneal entrance pupil reconstruction process can be performed 906 (which can be the stereo-limbal-corneal entrance pupil reconstruction process 500 of FIG. 5). If the effective count of limbus features is less than two, a stereo-corneal entrance pupil reconstruction process can be performed 908 (which can be the stereo-corneal entrance pupil reconstruction process 400 of FIG. 4).

Returning back to step 902, If the effective count of pupil features is less than two, a class of mono processes is implemented. The decision process continues with a determination of the effective count of limbus features 910. If the effective count of limbus features is at least one, a mono-limbus-corneal entrance pupil reconstruction process can be performed 912. If the effective count of limbus features is zero, a mono-corneal entrance pupil reconstruction process can be performed 914 (which can be the mono-corneal entrance pupil reconstruction process 600 of FIG. 6).

Figure 10:
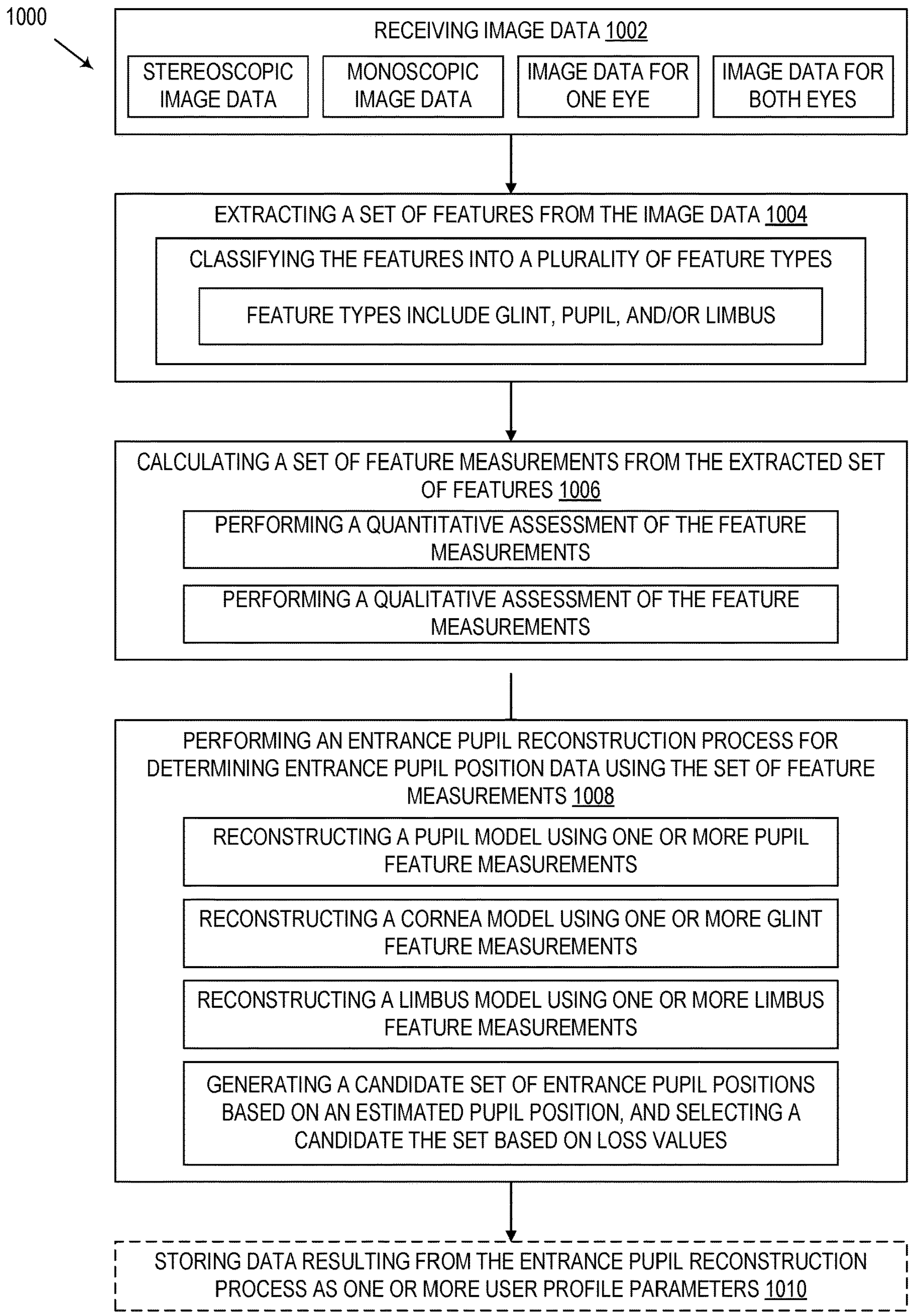
FIG. 10 shows a flow diagram of an example method for converting image data into entrance pupil position data, which can be implemented using the example display system of FIG. 1.

FIG. 10 shows a flow diagram of an example method 1000 for converting image data into entrance pupil position data. The method 1000 includes, at step 1002, receiving image data. The image data can be received and provided in various ways. The image data can include images of one or both of the user's eyes. In some implementations, the image data is received from a camera system having two cameras for imaging each of the user's eyes (i.e., a total of at least four cameras). In such cases, the image data can include stereoscopic image data, which can include multiple images of the same eye captured from different perspectives. The image data can also be received from a camera system with only a single camera for imaging each of the user's eyes (i.e., a total of two cameras). In such cases, the image data can one mono-view image for any given eye.

At step 1004, the method 1000 includes extracting a set of features from the image data. For image data containing multiple images, the feature extraction process can be performed for each image in the image data. Example feature extraction processes include image segmentation neural networks, edge detection, shape detection, and image thresholding. The extracted set of features can be classified into a plurality of feature types. Example feature types can include but are not limited to glint, pupil, and limbus feature types. Feature types of other eye features may also be utilized. The features can be classified using various processes, including but not limited to use of a neural network for classifying extracted features.

At step 1006, the method 1000 includes calculating a set of feature measurements from the extracted set of features. Calculating a set of feature measurements can include performing a quantity assessment and/or a quality assessment. The quantity assessment can include performing a count of each feature type. The quality assessment can be performed to provide confidence information used to determine whether the feature measurement is reliable. In some implementations, the quality assessment provides confidence information used to determine an effective count of each feature type. For each feature measurement failing a predefined confidence threshold level, a deduction in the count of the corresponding feature type is made. The effective count for each feature type can be used to determine which entrance pupil reconstruction process to perform.

At step 1008, the method 1000 includes performing an entrance pupil reconstruction process for determining entrance pupil position data using the set of feature measurements. The entrance pupil reconstruction process can be performed in various ways. Depending on the feature measurements and feature types that are available for processing, different methodologies can be implemented. For example, the process can include reconstructing a pupil model using one or more pupil feature measurements. A cornea model can be reconstructed using one or more glint feature measurements, and a limbus model can be reconstructed using one or more limbus feature measurements. Different effective counts of feature types can affect which entrance pupil reconstruction process is to be performed.

In some implementations, the feature measurements provided include only one pupil feature measurement for a given eye. In such cases, a mono-entrance pupil reconstruction process can be performed. In some implementations, the process includes estimating a pupil position using the one pupil feature measurement provided. The estimated pupil position can be used to generate a candidate set of entrance pupil positions. The candidate can be selected in various ways. For example, a loss function can be applied to the candidate set of entrance pupil positions, and the resulting loss values can be evaluated. In some implementations, the candidate with the lowest loss value is selected.

At step 1010, the method 1000 optionally includes storing data resulting from the entrance pupil reconstruction process as one or more user profile parameters. For example, parameters related to eye features that were calculated during performance of the processes described herein can be saved to a database that stores such parameters for a given user. The stored parameters can be retrieved as needed in future entrance pupil reconstruction processes. For example, limbus features may be missing from image data received during a future process. In such cases, parameters relating to limbus features for the given user can be used in the entrance pupil reconstruction process.

The processes described herein provide robust methods for implementing entrance pupil reconstruction without relying on assumed parameters of the user's eye(s). Such methodologies enable coverage of a larger population as assumed parameters generally only apply well to users with average eye features, such as average pupil sizes. In the processes described herein, image data of one or both of the user's eyes can be utilized to estimate an entrance pupil position. Features extracted and analyzed from the image data provides a more accurate method compared to those that utilizes average parameter values. In cases where the image data do not provide sufficient features, remaining parameters can be assumed.

In some embodiments, the methods and processes described herein may be tied to a computing system of one or more computing devices. In particular, such methods and processes may be implemented as a computer-application program or service, an application-programming interface (API), a library, and/or other computer-program product.

Figure 11:
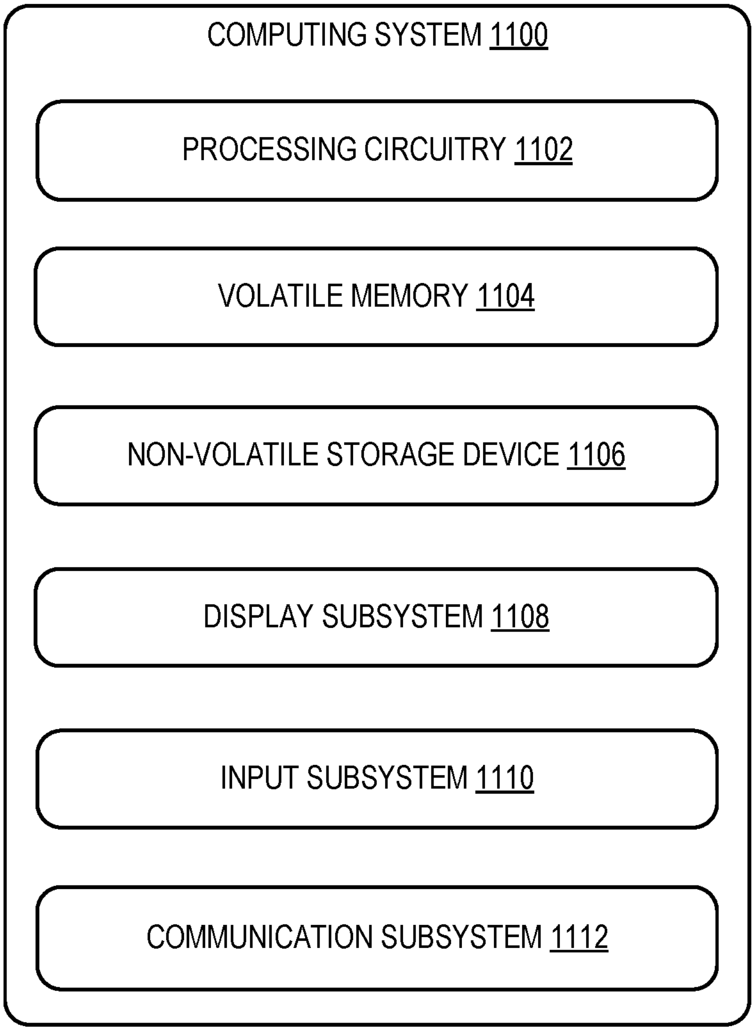
FIG. 11 shows a schematic view of an example computing environment in which the computer device of FIG. 1 may be enacted.

FIG. 11 schematically shows a non-limiting embodiment of a computing system 1100 that can enact one or more of the methods and processes described above. Computing system 1100 is shown in simplified form. Computing system 1100 may embody the computing system 100 described above and illustrated in FIG. 1, respectively. Components of computing system 1100 may be included in one or more personal computers, server computers, tablet computers, home-entertainment computers, network computing devices, video game devices, mobile computing devices, mobile communication devices (e.g., smartphone), and/or other computing devices, and wearable computing devices such as smart wristwatches and head mounted augmented reality devices.

Computing system 1100 includes processing circuitry 1102, volatile memory 1104, and a non-volatile storage device 1106. Computing system 1100 may optionally include a display subsystem 1108, input subsystem 1110, communication subsystem 1112, and/or other components not shown in FIG. 11.

Processing circuitry typically includes one or more logic processors, which are physical devices configured to execute instructions. For example, the logic processors may be configured to execute instructions that are part of one or more applications, programs, routines, libraries, objects, components, data structures, or other logical constructs. Such instructions may be implemented to perform a task, implement a data type, transform the state of one or more components, achieve a technical effect, or otherwise arrive at a desired result.

The logic processor may include one or more physical processors configured to execute software instructions. Additionally or alternatively, the logic processor may include one or more hardware logic circuits or firmware devices configured to execute hardware-implemented logic or firmware instructions. Processors of the processing circuitry 1102 may be single-core or multi-core, and the instructions executed thereon may be configured for sequential, parallel, and/or distributed processing. Individual components of the processing circuitry optionally may be distributed among two or more separate devices, which may be remotely located and/or configured for coordinated processing. For example, aspects of the computing system disclosed herein may be virtualized and executed by remotely accessible, networked computing devices configured in a cloud-computing configuration. In such a case, these virtualized aspects are run on different physical logic processors of various different machines, it will be understood. These different physical logic processors of the different machines will be understood to be collectively encompassed by processing circuitry 1102.

Non-volatile storage device 1106 includes one or more physical devices configured to hold instructions executable by the processing circuitry to implement the methods and processes described herein. When such methods and processes are implemented, the state of non-volatile storage device 1106 may be transformed—e.g., to hold different data.

Non-volatile storage device 1106 may include physical devices that are removable and/or built in. Non-volatile storage device 1106 may include optical memory, semiconductor memory, and/or magnetic memory, or other mass storage device technology. Non-volatile storage device 1106 may include nonvolatile, dynamic, static, read/write, read-only, sequential-access, location-addressable, file-addressable, and/or content-addressable devices. It will be appreciated that non-volatile storage device 1106 is configured to hold instructions even when power is cut to the non-volatile storage device 1106.

Volatile memory 1104 may include physical devices that include random access memory. Volatile memory 1104 is typically utilized by processing circuitry 1102 to temporarily store information during processing of software instructions. It will be appreciated that volatile memory 1104 typically does not continue to store instructions when power is cut to the volatile memory 1104.

Aspects of processing circuitry 1102, volatile memory 1104, and non-volatile storage device 1106 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module," "program," and "engine" may be used to describe an aspect of computing system 1100 typically implemented in software by a processor to perform a particular function using portions of volatile memory, which function involves transformative processing that specially configures the processor to perform the function. Thus, a module, program, or engine may be instantiated via processing circuitry 1102 executing instructions held by non-volatile storage device 1106, using portions of volatile memory 1104. It will be understood that different modules, programs, and/or engines may be instantiated from the same application, service, code block, object, library, routine, API, function, etc. Likewise, the same module, program, and/or engine may be instantiated by different applications, services, code blocks, objects, routines, APIs, functions, etc. The terms "module," "program," and "engine" may encompass individual or groups of executable files, data files, libraries, drivers, scripts, database records, etc.

When included, display subsystem 1108 may be used to present a visual representation of data held by non-volatile storage device 1106. The visual representation may take the form of a GUI. As the herein described methods and processes change the data held by the non-volatile storage device, and thus transform the state of the non-volatile storage device, the state of display subsystem 1108 may likewise be transformed to visually represent changes in the underlying data. Display subsystem 1108 may include one or more display devices utilizing virtually any type of technology. Such display devices may be combined with processing circuitry 1102, volatile memory 1104, and/or non-volatile storage device 1106 in a shared enclosure, or such display devices may be peripheral display devices.

When included, input subsystem 1110 may comprise or interface with one or more user-input devices such as a keyboard, mouse, touch screen, camera, or microphone.

When included, communication subsystem 1112 may be configured to communicatively couple various computing devices described herein with each other, and with other devices. Communication subsystem 1112 may include wired and/or wireless communication devices compatible with one or more different communication protocols. As non-limiting examples, the communication subsystem may be configured for communication via a wired or wireless local- or wide-area network, broadband cellular network, etc. In some embodiments, the communication subsystem may allow computing system 1100 to send and/or receive messages to and/or from other devices via a network such as the Internet.

The following paragraphs provide additional description of the subject matter of the present disclosure. One aspect provides a device for reconstructing entrance pupils, the device comprising a camera system and processing circuitry coupled to memory storing instructions that, when executed by the processing circuitry, causes the processing circuitry to receive image data from the camera system, extract a set of features from the image data, wherein extracting the set of features comprises classifying the features into a plurality of feature types, calculate a set of feature measurements from the extracted set of features, and perform an entrance pupil reconstruction process for determining entrance pupil position data using the set of feature measurements. In this aspect, additionally or alternatively, the camera system comprises a first camera for capturing images of a first eye of a user and a second camera for capturing images of a second eye of the user, and wherein the entrance pupil position data comprises a first entrance pupil position for the first eye and a second entrance pupil position for the second eye. In this aspect, additionally or alternatively, the camera system comprises a first camera and a second camera for capturing images of a first eye of a user, and wherein the received image data comprises stereoscopic image data of the first eye. In this aspect, additionally or alternatively, the set of features measurements comprises one or more pupil feature measurements, performing the entrance pupil reconstruction process comprises reconstructing a pupil model using the one or more pupil feature measurements, and the entrance pupil position data is determined based on a ray-tracing process using the pupil model. In this aspect, additionally or alternatively, the set of features measurements further comprises one or more glint feature measurements, performing the entrance pupil reconstruction process further comprises reconstructing a cornea model using the one or more glint feature measurements, and the pupil model is reconstructed further using the cornea model. In this aspect, additionally or alternatively, the set of features measurements further comprises one or more limbus feature measurements, and performing the entrance pupil reconstruction process further comprises reconstructing a limbus model using the one or more limbus feature measurements and reconstructing a cornea refractive index based on the limbus model and the pupil model, wherein the entrance pupil position data is determined further based on the cornea refractive index. In this aspect, additionally or alternatively, the set of feature measurements comprises a pupil feature measurement, and wherein performing the entrance pupil reconstruction process comprises estimating a pupil position based on the pupil feature measurement, determining a set of candidate entrance pupil positions based on the estimated pupil position, and selecting a candidate entrance pupil position from the set of candidate entrance pupil positions based on loss values resulting from applying a loss function to each of the candidate entrance pupil positions. In this aspect, additionally or alternatively, the set of feature measurements further comprises a limbus feature measurement, and wherein the pupil position is estimated based on the limbus feature measurement. In this aspect, additionally or alternatively, performing the entrance pupil reconstruction process comprises using one or more user profile parameters to compensate for missing feature measurements. In this aspect, additionally or alternatively, the instructions, when executed by the processing circuitry, further causes the processing circuitry to store data resulting from the entrance pupil reconstruction process as one or more user profile parameters.

Another aspect includes a method for reconstructing entrance pupils, the method comprising receiving image data, extracting a set of features from the image data, wherein extracting the set of features comprises classifying the features into a plurality of feature types, calculating a set of feature measurements from the extracted set of features, and performing an entrance pupil reconstruction process for determining entrance pupil position data using the set of feature measurements. In this aspect, additionally or alternatively, the received image data comprises at least one image of a first eye of a user and at least one image of a second eye of the user, and wherein the entrance pupil position data comprises a first entrance pupil position for the first eye and a second entrance pupil position for the second eye. In this aspect, additionally or alternatively, the received image data comprises stereoscopic images of a first eye of a user. In this aspect, additionally or alternatively, the set of features measurements comprises one or more pupil feature measurements and one or more glint feature measurements, performing the entrance pupil reconstruction process comprises reconstructing a cornea model using the one or more glint feature measurements and reconstructing a pupil model using the one or more pupil feature measurements and the cornea model, and the entrance pupil position data is determined based on a ray-tracing process using the pupil model. In this aspect, additionally or alternatively, the set of features measurements further comprises one or more limbus feature measurements, and performing the entrance pupil reconstruction process further comprises reconstructing a limbus model using the one or more limbus feature measurements and reconstructing a cornea refractive index based on the limbus model and the pupil model, wherein the entrance pupil position data is determined further based on the cornea refractive index. In this aspect, additionally or alternatively, the set of feature measurements comprises a pupil feature measurement, and wherein performing the entrance pupil reconstruction process comprises estimating a pupil position based on the pupil feature measurement, determining a set of candidate entrance pupil positions based on the estimated pupil position, and selecting a candidate entrance pupil position from the set of candidate entrance pupil positions based on loss values resulting from applying a loss function to each of the candidate entrance pupil positions. In this aspect, additionally or alternatively, the set of feature measurements further comprises a limbus feature measurement, and wherein the pupil position is estimated based on the limbus feature measurement. In this aspect, additionally or alternatively, the method further includes storing data resulting from the entrance pupil reconstruction process as one or more user profile parameters.

Another aspect includes an extended reality device for reconstructing entrance pupils, the device comprising a camera system and processing circuitry coupled to memory storing instructions that, when executed by the processing circuitry, causes the processing circuitry to receive image data from the camera system, extract a set of features from the image data, wherein extracting the set of features comprises classifying the features into a plurality of feature types, perform a feature measurement process to calculate a set of feature measurements, the feature measurement process comprising performing a quantity assessment on the features for each of the feature types and performing a quality assessment for each of the features, select a process from a set of entrance pupil reconstruction processes to be performed based on the set of feature measurements, and perform the selected process. In this aspect, additionally or alternatively, the plurality of feature types comprises a glint feature type, a pupil feature type, and a limbus feature type, performing the quality assessment for each of the features result in an effective count for each of the feature types, and the selected process is selected based on, upon determining that the effective count for the pupil feature type is below a predetermined threshold number, the selected process is a mono-based entrance pupil reconstruction process, and, upon determining that the effective count for the pupil feature type is above a predetermined threshold number, the selected process is a stereo-based entrance pupil reconstruction process.

"And/or" as used herein is defined as the inclusive or V, as specified by the following truth table:

| A | B | $A \vee B$ |
|---|---|---|
| True | True | True |
| True | False | True |
| False | True | True |
| False | False | False |

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A device for reconstructing entrance pupils, the device comprising:

a camera system; and processing circuitry coupled to memory storing instructions that, when executed by the processing circuitry, causes the processing circuitry to:

receive image data from the camera system;

extract a set of features from the image data, wherein extracting the set of features comprises classifying the features into a plurality of feature types;

calculate a set of feature measurements from the extracted set of features, wherein calculating the set of feature measurements comprises determining an effective count for each of the plurality of feature types; and perform an entrance pupil reconstruction process for determining entrance pupil position data using the set of feature measurements, wherein the entrance pupil reconstruction process is a mono-based entrance pupil reconstruction process or a stereo-based entrance pupil reconstruction process selected based on the effective counts for the plurality of feature types.

2. The device of claim 1, wherein the camera system comprises a first camera for capturing images of a first eye of a user and a second camera for capturing images of a second eye of the user, and wherein the entrance pupil position data comprises a first entrance pupil position for the first eye and a second entrance pupil position for the second eye.

3. The device of claim 1, wherein the camera system comprises a first camera and a second camera for capturing images of a first eye of a user, and wherein the received image data comprises stereoscopic image data of the first eye.

4. The device of claim 1, wherein:

the set of features measurements comprises one or more pupil feature measurements;

performing the entrance pupil reconstruction process comprises reconstructing a pupil model using the one or more pupil feature measurements; and the entrance pupil position data is determined based on a ray-tracing process using the pupil model.

5. The device of claim 4, wherein:

the set of features measurements further comprises one or more glint feature measurements;

performing the entrance pupil reconstruction process further comprises reconstructing a cornea model using the one or more glint feature measurements; and the pupil model is reconstructed further using the cornea model.

6. The device of claim 4, wherein:

the set of features measurements further comprises one or more limbus feature measurements; and performing the entrance pupil reconstruction process further comprises:

reconstructing a limbus model using the one or more limbus feature measurements; and reconstructing a cornea refractive index based on the limbus model and the pupil model, wherein the entrance pupil position data is determined further based on the cornea refractive index.

7. The device of claim 1, wherein the set of feature measurements comprises a pupil feature measurement, and wherein performing the entrance pupil reconstruction process comprises:

estimating a pupil position based on the pupil feature measurement;

determining a set of candidate entrance pupil positions based on the estimated pupil position; and selecting a candidate entrance pupil position from the set of candidate entrance pupil positions based on loss values resulting from applying a loss function to each of the candidate entrance pupil positions.

8. The device of claim 7, wherein the set of feature measurements further comprises a limbus feature measurement, and wherein the pupil position is estimated based on the limbus feature measurement.

9. The device of claim 1, wherein performing the entrance pupil reconstruction process comprises using one or more user profile parameters to compensate for missing feature measurements.

10. The device of claim 1, wherein the instructions, when executed by the processing circuitry, further causes the processing circuitry to:

store data resulting from the entrance pupil reconstruction process as one or more user profile parameters.

11. A method for reconstructing entrance pupils, the method comprising:

receiving image data;

extracting a set of features from the image data, wherein extracting the set of features comprises classifying the features into a plurality of feature types;

calculating a set of feature measurements from the extracted set of features, wherein calculating the set of feature measurements comprises determining an effective count for each of the plurality of feature types; and performing an entrance pupil reconstruction process for determining entrance pupil position data using the set of feature measurements, wherein the entrance pupil reconstruction process is a mono-based entrance pupil reconstruction process or a stereo-based entrance pupil reconstruction process selected based on the effective counts for the plurality of feature types.

12. The method of claim 11, wherein the received image data comprises at least one image of a first eye of a user and at least one image of a second eye of the user, and wherein the entrance pupil position data comprises a first entrance pupil position for the first eye and a second entrance pupil position for the second eye.

13. The method of claim 11, wherein the received image data comprises stereoscopic images of a first eye of a user.

14. The method of claim 11, wherein:

the set of features measurements comprises one or more pupil feature measurements and one or more glint feature measurements;

performing the entrance pupil reconstruction process comprises reconstructing a cornea model using the one or more glint feature measurements and reconstructing a pupil model using the one or more pupil feature measurements and the cornea model; and the entrance pupil position data is determined based on a ray-tracing process using the pupil model.

15. The method of claim 14, wherein:

the set of features measurements further comprises one or more limbus feature measurements; and performing the entrance pupil reconstruction process further comprises:

reconstructing a limbus model using the one or more limbus feature measurements; and reconstructing a cornea refractive index based on the limbus model and the pupil model, wherein the entrance pupil position data is determined further based on the cornea refractive index.

16. The method of claim 11, wherein the set of feature measurements comprises a pupil feature measurement, and wherein performing the entrance pupil reconstruction process comprises:

estimating a pupil position based on the pupil feature measurement;

determining a set of candidate entrance pupil positions based on the estimated pupil position; and selecting a candidate entrance pupil position from the set of candidate entrance pupil positions based on loss values resulting from applying a loss function to each of the candidate entrance pupil positions.

17. The method of claim 16, wherein the set of feature measurements further comprises a limbus feature measurement, and wherein the pupil position is estimated based on the limbus feature measurement.

18. The method of claim 11, further comprising:

storing data resulting from the entrance pupil reconstruction process as one or more user profile parameters.

19. An extended reality device for reconstructing entrance pupils, the device comprising:

a camera system; and processing circuitry coupled to memory storing instructions that, when executed by the processing circuitry, causes the processing circuitry to:

receive image data from the camera system;

extract a set of features from the image data, wherein extracting the set of features comprises classifying the features into a plurality of feature types;

perform a feature measurement process to calculate a set of feature measurements, the feature measurement process comprising:

determining an effective count for each of the plurality of feature types;

select a process from a set of entrance pupil reconstruction processes to be performed based on the set of feature measurements, wherein the process is a mono-based entrance pupil reconstruction process or a stereo-based entrance pupil reconstruction process selected based on the effective counts for the plurality of feature types; and perform the selected process.

20. The extended reality device of claim 19, wherein:

the plurality of feature types comprises a glint feature type, a pupil feature type, and a limbus feature type; and the process is a limbus-corneal entrance pupil reconstruction process or a corneal entrance pupil reconstruction process selected based on the effective count of the limbus feature type.

* * * * *